(12) United States Patent
Sacks et al.

(10) Patent No.: US 10,555,906 B2
(45) Date of Patent: Feb. 11, 2020

(54) ORAL SOLID CANNABINOID FORMULATIONS, METHODS FOR PRODUCING AND USING THEREOF

(71) Applicants: GELPELL AG, Gahwil (CH); SATIPHARM AG, Cham (CH)

(72) Inventors: Hagit Sacks, Modi'in (IL); Tomas Edvinsson, Kirchberg (CH)

(73) Assignees: GELPELL AG, Gahwil (CH); SATIPHARM AG, Cham (CH)

(*) Notice: Subject to any disclaimer, the term of this patent is extended or adjusted under 35 U.S.C. 154(b) by 0 days.

(21) Appl. No.: 15/554,209

(22) PCT Filed: Feb. 9, 2017

(86) PCT No.: PCT/IL2017/050163
§ 371 (c)(1),
(2) Date: Aug. 28, 2017

(87) PCT Pub. No.: WO2017/137992
PCT Pub. Date: Aug. 17, 2017

(65) Prior Publication Data
US 2018/0078504 A1 Mar. 22, 2018

Related U.S. Application Data

(60) Provisional application No. 62/431,613, filed on Dec. 8, 2016, provisional application No. 62/294,006, filed on Feb. 11, 2016.

(51) Int. Cl.
*A61K 31/352* (2006.01)
*A61K 9/16* (2006.01)
*A61K 31/05* (2006.01)
*A61K 36/185* (2006.01)

(52) U.S. Cl.
CPC .......... *A61K 9/1658* (2013.01); *A61K 31/05* (2013.01); *A61K 31/352* (2013.01); *A61K 36/185* (2013.01)

(58) Field of Classification Search
CPC ....... C08L 89/06; A61K 45/06; A61K 9/1658; A61K 31/352; A61K 2300/00
See application file for complete search history.

(56) References Cited

U.S. PATENT DOCUMENTS

| 5,387,415 A | 2/1995 | Wunderlich et al. |
| 5,902,606 A | 5/1999 | Wunderlich et al. |
| 6,068,854 A | 5/2000 | Wunderlich et al. |
| 2002/0160043 A1* | 10/2002 | Coleman .............. A61K 9/0056 424/465 |
| 2007/0072939 A1* | 3/2007 | Kupper ................ A61K 31/353 514/454 |
| 2010/0330058 A1* | 12/2010 | Davis ................... A61K 9/0058 424/94.1 |
| 2014/0212453 A1* | 7/2014 | Chang ................... A23C 19/00 424/195.18 |

FOREIGN PATENT DOCUMENTS

| EP | 0 577 143 A2 | 1/1994 |
| WO | 2013/169101 A1 | 11/2013 |

OTHER PUBLICATIONS

Weeedchefs; online retrieved on Jan. 9, 2018 from: http://weedchefs.com/super-potent-cannabis-gummy-treats/; Dec. 2014:10 pages.*
Mary jane's jello shots; online retrieved on Jan. 9, 2018 from: https://www.michiganmedicalmarijuana.org/topic/40169-mary-janes-jello-shots/; May 2012:4 pages.*
Sigma aldich gelatin online retrieved on Jan. 9, 2018 from: https://web.archive.org/web/20141031133811/https://www.sigmaaldrich.com/content/dam/sigma-aldrich/docs/Sigma/Product_Information_Sheet/2/g9382pis.pdf; Oct. 2014; 3 pages.*
Lavanya et al. IJPSR 2011;2(6):1337-1355).*
Podczeck et al. (Pharmaceutical Capsules 2004 pp. 49 and 50).*
Tewari et al. (Mikrochimica Acta 1974, 991-995).*
Pellet definition; [online] retrieved on Jan. 9, 2018 from: https://www.merriam-webster.com/dictionary/pellet 1 page.*
What is Water Soluble CBD? [online] retrieved on May 7, 2018 from: https://discovercbd.com/blogs/cbd-news/what-is-water-soluble-cbd; May 2017; 4 pages. (Year: 2017).*
Shrewsbury (Applied Pharmaceutics in Contemporary Compounding Jan. 2015 pp. 140 and 150). 3 pages. (Year: 2015).*
Gagne et al. (PNAS 2012;109(31):12811-12816) (Year: 2012).*
English translation of Wolfgang WO 2007090393 2007; 8 pages. (Year: 2007).*
Atakan (Ther Adv Psychopharmacol 2012;2(6):241-254) (Year: 2012).*
Atsmon et al., "Single-Dose Pharmacokinetics of Oral Cannabidiol Following Administration of PTL101: A New Formulation Based on Gelatin Matrix Pellets Technology", Clinical Pharmacology in Drug Development, 2017, 00(0) 1-8.
Karschner et al., "Plasma Cannabinoid Pharmacokinetics Following Controlled Oral Δ9-Tetrahydrocannabinol and Oromucosal Cannabis Extract Administration", Clin Chem, Jan. 2011; 57(1): 66-75.

* cited by examiner

*Primary Examiner* — Ernst V Arnold
(74) *Attorney, Agent, or Firm* — Vorys, Sater, Seymour and Pease LLP

(57) ABSTRACT

Provided are solid oral/per os formulations that include a single cannabinoid, combination of cannabinoids, *cannabis* extract and combination of *cannabis* plant constituents. Also provided are methods of making the formulations, as well as therapeutic applications in the treatment and alleviation of various human disorders and/or conditions.

20 Claims, 3 Drawing Sheets

ORAL SOLID CANNABINOID FORMULATIONS, METHODS FOR PRODUCING AND USING THEREOF

TECHNOLOGICAL FIELD

The invention generally provides oral/per os solid formulations and encapsulation technique comprising single cannabinoid, combination of cannabinoids, *cannabis* extract and combination of *cannabis* plant constituents.

BACKGROUND

The use of *cannabis* and cannabinoids for medical purposes has been gaining increased interest in recent years. There is a growing body of evidence that *cannabis* may have a beneficial impact on clinical conditions such as pain (e.g. cancer pain, fibromyalgia related pain, neuropathic pain), inflammatory diseases (e.g. inflammatory bowel diseases, Crohn's disease, ulcerative colitis), posttraumatic stress disorder (PTSD), loss of appetite/anorexia, sleep disorders, symptoms of multiple sclerosis (MS), epilepsy, autism, schizophrenia, and other disorders. The principal active components of *cannabis* plant that modulate the human endocannabinoid system are delta-9-tetrahydrocannabinol (THC) and cannabidiol (CBD). Similarly to the endocannabinoids, anandamide and 2-AG, THC can activate both CB1 and CB2 receptors exerting a wide variety of biological effects by mimicking these endocannabinoids. In contrast to THC, CBD has a relatively low affinity for CB1 and CB2 receptors. However, several groups have recently shown that CBD antagonizes cannabinoid agonists, indicating that CBD can interact with cannabinoid CB1 and CB2 receptors.

THC is a psychoactive substance that accounts for the therapeutic effect as well as some adverse events. THC effects include, antiemetic properties, mild to moderate analgesic effects, relaxation, alteration of visual, auditory, and olfactory senses, and fatigue. CBD, a major non-psychotropic constituent of *cannabis*, has multiple pharmacological actions, including anticonvulsant, anxiolytic, antipsychotic, antiemetic, sedative, anti-inflammatory, anti-epileptic, anti-oxidative and neuro-protective actions. Moreover, it is thought to alleviate the untoward psychotropic effects of THC. The multiple mechanism of action of CBD support its possible therapeutic effects in many diseases, e.g. MS, Parkinson's disease, Alzheimer's disease, cerebral ischemia, diabetes, rheumatoid arthritis, nausea and cancer.

The rationale for using a combination of the two cannabinoids stems from the reports in the scientific literature that CBD could not only potentiate the therapeutic effects of THC, but also diminish the undesirable effects of THC, such as anxiety, panic, sedation, dysphonia and tachycardia. Additionally, co-administration of THC and CBD was reported to be safe with no tolerance, abuse or withdrawal effects. Therefore, a pharmaceutical dosage form that combines the two active cannabinoids and enables efficient delivery is most desirable.

There are only few *cannabis*-based drug products, which are either approved for marketing as drugs or are in their last stages of development, which are manufactured under more strict good manufacturing practice requirements for pharmaceuticals. The first *cannabis*-based medicine was Marinol®, a synthetic THC (dronabinol), formulated in sesame oil in oral soft gelatin capsules. It is indicated for treatment of cachexia in patients with AIDS, and nausea and vomiting associated with cancer chemotherapy in patients who have failed to adequately respond to conventional antiemetic treatments. Among its drawbacks are poor bioavailability, high inter- and intra-subject variability, and other THC related side effects. Therefore, its compliance and use are relatively limited. Another currently marketed cannabinoids-based drug is Sativex®, initially indicated for symptomatic treatment in MS. It is a buccal spray formulated in ethanol, propylene glycol, and peppermint oil. It is administered onto the oromucosal surface and therefore claims to bypass the 'first pass' metabolism of cannabinoids associated with intestinal absorption. However, a number of adverse events experienced with Sativex limit its use. Sativex formulation contains excipients that following continuous use often lead to lesions, mouth ulcerations, pain and soreness of the oral mucosa. In such cases, the treatment has to be interrupted until complete healing of the oral mucosa occurs. In addition, the pharmacokinetic data of Sativex showed great intra and inter subject variability following single and repeated dosing. In terms of clinical practice, the highly variable and erratic pharmacokinetic profiles of this product leads to increased daily usage nearly by 3-fold, and compliance of patients to such frequent daily dosage is usually poor.

An optimal oral dosage form of cannabinoids is not yet available due to the substantial 'first pass' metabolic effect which limits the oral bioavailability of cannabinoids to 6% [1]. Currently, medical *cannabis* is administered primarily through smoking or, alternatively, consumed orally in the form of oil, cookies, chocolates, etc. The majority of these products are not standardized, i.e. cannabinoids composition and doses are uncontrolled, and demonstrate major disadvantages of poor bioavailability resulting in administration of very high cannabinoid doses and increased side effects, high dosing frequency, high variability, low patient compliance, and short product self-life due to formulation instability.

Certain gelatin-based formulations comprising active ingredients other than cannabinoids have been described in U.S. Pat. Nos. 5,387,415 [2], 5,902,606 [3] and 6,068,854 [4].

REFERENCES

[1] Karschner E L, Darwin W D, Goodwin R S, Wright S, Huestis M A. Plasma Cannabinoid Pharmacokinetics Following Controlled Oral Δ9-Tetrahydrocannabinol and Oromucosal *Cannabis* Extract Administration. Clin Chem 2011 January; 57(1): 66-75.
[2] U.S. Pat. No. 5,387,415.
[3] U.S. Pat. No. 5,902,606.
[4] U.S. Pat. No. 6,068,854.

GENERAL DESCRIPTION

The need for effective oral delivery of *cannabis* and cannabinoids, especially THC and CBD, is essential for the development of therapeutic strategy to maximize therapeutic effects, to increase patient compliance and to obtain stable and predictable plasma drug levels and, as a consequence, reproducible pharmacodynamics and therapeutics effects.

The present invention thus provides a family of products and method of manufacture involving a unique technology that is associated with the preparation and use of gelatin matrix-pellets tailored for obtaining high loading, high compliance, user friendly cannabinoids and *cannabis*-based medicines. Due to its particular advantageous features, the present technology enables to achieve incorporation of high amounts of active ingredient(s), capability to incorporate one active or several ingredients in one single pellet or in different pellets that are mixed or formulated into capsule forms, enabling multi-dose platform. The pellets or capsule used for packaging can be gastro resistant by addition of entro-coating.

The technology further enables to obtain high bioavailability that contributes to improved dosing efficiency and frequency, with no delivery system side effects. Moreover, the process demonstrate dose proportionality, as observed in the active ingredient blood levels, in at least ten-fold range, allowing the clinician to personalize the dose for each patient by choosing the capsules numbers required per day.

More specifically, the scope of the technology is that it allows dose titration and personalized medicine. Various doses and cannabinoids combinations can be produced as each single bead stands for itself, and a final dose is determined by packaging a suitable amount of beads and/or by mixing a suitable amount of beads from each type (e.g. CBD and THC beads are mixed to achieve a specific combination and dose). The preparation can be done on-demand by stocking various bead types and mixing the amount required from each type when desired. Alternatively, beads can be prepared with more than one cannabinoid in the same bead. This personalized approach can be further extended to incorporate additional nutrients and therapeutic agents. This approach is especially useful for medical indications using cannabinoids or *cannabis*-based medicines as add-on therapy. Furthermore, this approach permits to combine both water soluble and lipophilic drugs in a single capsule, and further together with *cannabis* derived medicines.

The obtained gelatin matrix pellets (also referred to herein as beadlets or beads) comprising cannabinoids or *cannabis*-based constituents constitute an advantageous and advanced oral dosage form for these and potentially other lipophilic active ingredients. The active ingredients are homogenously distributed in the solid matrix and fully inter-mixed therein, thereby being essentially protected in a three-dimensional gelatin matrix, which does not need a shell or an additional filling material. A plurality of these compact matrix pellets can be packed into, e.g., two-piece hard capsules, including an external gastro-resistant coating, if desired. The gelatin pellets unique manufacturing process enables the formation of seamless homogenous beads that fulfill the strict requirements for pharmaceutical dosage forms. It should be noted that this unique manufacturing process, as detailed further below, does not involve any compression or centrifugation step.

In addition, gelatin pellets of the invention may be various and selected amongst a great variety of available capsules. For examples, gelatin pellets may be used that are smell-free, genetically modified organism (GMO)-free, preservative-free, not irradiated, allergen-free, gluten-free and/or lactose-free. The gelatin matrix may be 100% natural and made of a digestible gelatin polymer (fish or bovine) that is readily soluble in the body temperature (in less than 30 minutes). In the aqueous environment of the gastrointestinal (GI) tract, this soluble gelatin polymer promotes dispersion of lipophilic cannabinoids and thereby enhances bioavailability of the active ingredients. In terms of number and size, a plurality of gelatin matrix pellets dispense over the whole GI system, thus enabling to achieve a relatively constant GI-transit time, which makes them essentially distinct from single-unit-dosage-forms, like tablets or soft gelatin capsules. This particular feature helps to avoid punctual irritation of gastric mucosa and makes them more tolerable. A maximized surface to volume ratio is another contributor to enhanced bioavailability, which ensures a uniform release of the active ingredients.

Cannabinoids are lipophilic and highly hydrophobic molecules. Moreover, ambient light and temperature increase degradation of delta-9-THC and CBD, and subsequently, increase the degree of formation of CBN (cannabinol). This imposes significant limitations on achieving successful pharmaceutical formulations of cannabinoids, in both liquid and solid forms, in terms of solubility, stability and uniform delivery of pharmaceutical actives.

Despite known advantages of liquid pharmaceutical compositions (e.g., easy to swallow, uniform delivery and rapid onset), preparation of such compositions is not always achievable for certain desired pharmaceutical actives. Poorly soluble actives, such as cannabinoids, may require relatively large volumes of solvents, while the choice of solvents is limited by safety, compatibility, stability, and economic concerns. Furthermore, use of large volumes of solvents for solubilizing pharmaceutical actives is undesirable, because such solutions would be so dilute as to require impractically large dosages for delivering a therapeutically effective amount of active.

In the preparation of solid or compressed formulations, which are meant to overcome these disadvantages, dissolution of pharmaceutical actives is a critical problem. One approach to overcome the solubility problem has been to incorporate water, water-miscible co-solvents, and surfactants into the formulations, such as aqueous solutions of polyethylene glycol, mixtures of polyethylene glycol and surfactants, and mixtures of polyethylene glycol and alcohols, and further additions of polyvinylpyrrolidone and acrylic acid resin, at controlled pH, with an ionized or partly-ionized pharmaceutical active. In many instances, however, incorporation of water or water-miscible co-solvents or surfactants into a pharmaceutical composition is not possible or desirable. For example, water-miscible co-solvents, such as ethanol, have the disadvantage of being relatively volatile, thereby resulting in concentration changes in the actives over time. Further, these co-solvents may be incompatible with the desired pharmaceutical actives. One particular disadvantage is that water and volatile water-miscible co-solvents are incompatible with formulations such as soft gelatin capsules. Even though it may be possible to prepare soft gelatin capsules containing these solvents, over time the capsules gradually soften and deform, and develop leaks as these solvents dissolve the soft gelatin shell. It would be therefore highly desirable to develop a preparation process which will not require the use of water or water-miscible co-solvents.

More specifically, THC and CBD due to their sensitivity to oxidation, hydrolysis, thermal, and photolytic degradation make the design of cannabinoid formulations particularly challenging. THC and CBD usually require solubilization with either a surfactant or adherence to a water miscible substance (e.g., albumin, Tween 80, Emulphor). Sativex, for example, a commercial preparation of a *cannabis* extract containing THC and CBD at 1:1 ratio, further contains organic solvents such as propylene glycol and ethanol that have been associated with its significant side effects. Epidiolex, a more recent CBD liquid formulation still under clinical trials, contains oil and ethanol in order to achieve sufficient solubility.

Further, even when dissolved in these vehicles, THC and CBD have limited solubility and will precipitate if care is not exercised. They have tendency to adhere to solid surfaces rather than remain in solution under certain conditions.

There is always the concern that different vehicles may influence the pharmacological effects of THC and CBD. In case of cannabinoids extracts, there is a significant issue of bad taste when administered as oral, sublingual, and buccal medications. This is especially true for liquid cannabinoid formulations, such as Sativex, leading to reduced compliance in patients treated with these drugs. Solubility is also an important parameter affecting drug permeation across biological membranes.

The present inventors have surprisingly found a straightforward and reproducible method for preparing a novel solid homogeneous formulation of the highly hydrophobic cannabinoids (e.g., CBD) in an admissible size and form, with relatively high load of actives and low water content, and furthermore exempt of water-miscible co-solvents such as alcohol, exempt of surfactants, and exempt of fillers. The novel compositions of the invention, comprising active and non-active ingredients are conferred with surprising and advantageous properties, i.e., improved stability, recovery of an active, uniformity and shelf life, and further with improved pharmacokinetic and pharmacodynamic indices in clinical trials and in quality control studies.

Achieving an effective oral delivery of cannabinoids is essential in the strategy to maximize their therapeutic effects, to increase patient compliance, and to obtain stable and predictable plasma drug levels and, as a consequence, reproducible pharmacodynamic effects. However, effective oral formulations of cannabinoids has proven to be particularly difficult, due to their limited solubility in plasma, limited ability to cross biological membranes, P-glycoprotein 1 (P-gp) effect and first pass metabolism. Cannabinoid formulations that overcome these limitations in the sense of making the active agents available in the blood circulation, should have the capacity to dissolve or disperse the active agents to the level they can cross biological membranes and protect the agents from being metabolized or expelled via efflux from the enterocytes back to the GI lumen by efflux pumps such as P-gp. The present inventors have developed a process for making an improved formulation of cannabinoids, with proven added value in terms of enhanced stability and bioavailability, this latter value demonstrated to include controlled release and gastro-resistance.

Validity of the present technology in terms of enhanced solubility and oral bioavailability of CBD in the form of gelatin matrix pellets has been proven in Phase I human clinical study vis-à-vis the commercial reference formulation (Sativex). These findings are surprising in view of known limitations of intestinal absorption of cannabinoids in terms of poor water solubility, intestinal and hepatic first-phase metabolism by phase I metabolic enzymes (oxidative), intra-enterocytes phase II metabolic enzymes (glucuronidation), P-gp effect. These findings further imply that cannabinoid formulations according to the invention may have a less variable absorption at the GI tract, and thereby may lead to reduction of the therapeutically active dose.

From yet another point of view, the matrix pellets, e.g., gelatin formed, of the invention provide an advantageous dosage form for therapeutic uses. The beads are easy to dose for the various range of therapeutic indications using cannabinoids and *cannabis*-based medicines. They can easily be filled into capsules, sticks or sachets or can be consumed directly with food. The beads are easy to handle, easy to swallow (in a capsule or without). Further, this technology enables to achieve unique dosage forms comprising combinations of pellets from various sources and various combinations of cannabinoids. Ultimately, this technology may be applied to other lipophilic active ingredients.

BRIEF DESCRIPTION OF FIGURES

The following figures demonstrate certain advantageous features of the present invention. It is stressed that the particulars shown are by way of example and for purposes of illustrative discussion of the embodiment of the invention.

DETAILED DESCRIPTION OF EMBODIMENTS

Figure 1:
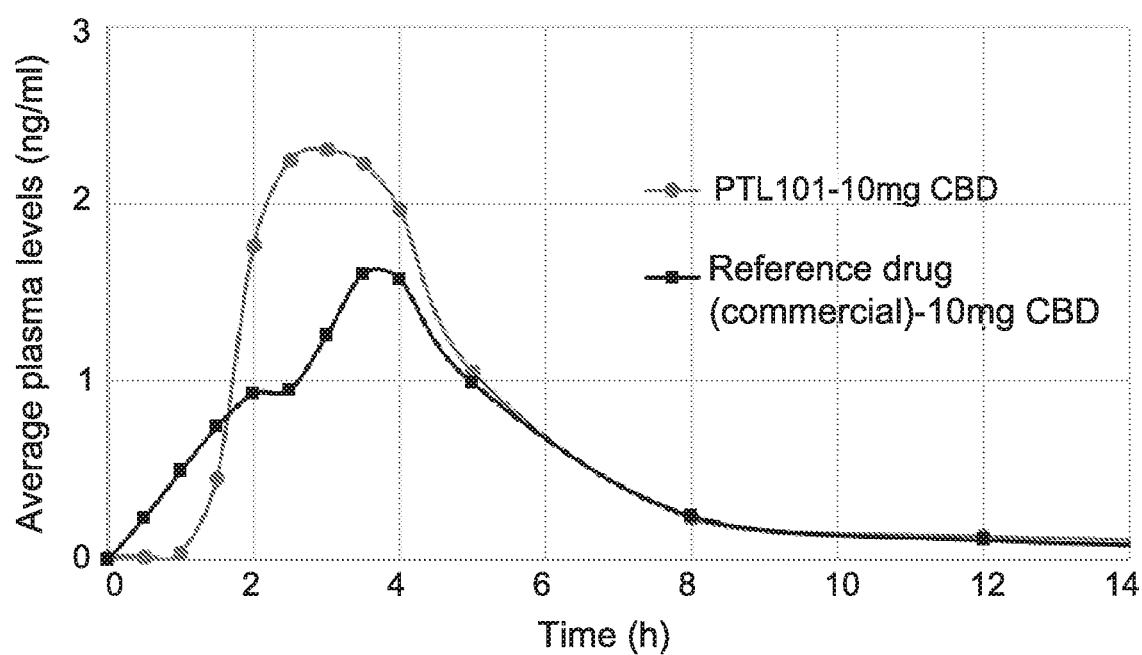
FIG. 1 demonstrates pharmacokinetic superiority of CBD gelatin matrix pellets of the invention (PTL101) compared to a commercial reference (Sativex), as revealed in mean CBD plasma levels following oral administering to healthy volunteers (N=14). CBD gelatin matrix pellets/PTL101 (grey curve), reference (black curve), both containing 10 mg CBD.

By describing specific embodiments of the invention it is not meant that this invention is limited to particular methods, and experimental conditions described, as such methods and conditions may vary. The terminology used herein is for the purpose of describing particular embodiments only, and is not intended to be limiting.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described.

Thus, in one of its main aspects the invention provides a matrix pellet, e.g., a gelatin matrix pellet, comprising a pre-defined amount of an active ingredient comprising at least one synthetic, semi-synthetic or natural cannabinoid, an extract of a *cannabis* plant, a combination of *cannabis* plant constituents, or a combination thereof. In other words, the invention provides a particular solid formulation of cannabinoids from synthetic, semi-synthetic or natural sources in the form of, e.g., compact gelatin matrix pellets (also beads), in particular with no shell and no additional (or a minimum) filling material.

A matrix pellet of the invention may be construed as a solid material composition comprising a matrix in which the active ingredient (a synthetic, semi-synthetic or natural cannabinoid, an extract of a *cannabis* plant, a combination of *cannabis* plant constituents, or a combination thereof) is carried, contained or comprised in a predefined amount. A matrix pellet of the invention may be further construed as a continuous material in which the active ingredient is homogenously dispersed.

In certain embodiments, the composition of a matrix pellet of the invention may be described as comprising a gelatin (e.g. fish or bovine), where the matrix is of gelatin or an alternative material in case the matrix is not gelatin, an oil (e.g. linseed oil, hemp oil, sesame oil, olive oil, castor oil, chia (Salvia hispanica L.) seed oil, cotton oil, corn oil, coconut oil, triglycerides, sunflower oil, soybean oil, canola oil, etc), a coloring agent (optional), water and a pre-defined amount of a cannabinoid (single or as a combination, and/or a cannabis plant extract, cannabis plant constituents, and/or a combination thereof. A matrix pellet may be coated with a gastro-resistant coating, using GRAS-based materials. A plurality of these matrix pellets can be packed, e.g., in a seamless two-piece hard capsule, further including an external gastro-resistant coating, if desired, thus providing a solid cannabinoid dosage form. Specific examples of matrix pellets of the invention, particularly those comprising various pre-defined amounts of the cannabinoid CBD and their specific pharmacokinetic properties are presently described.

In some embodiments, the matrix material is gelatin. It should be appreciated that in certain embodiments a gelatin pellet may comprise a gelatin of bovine or fish origin, characterized in terms of certain Bloom strength (defined as known in the art).

In some embodiments, gelatin Bloom which is applicable to the invention can be in the range of 100 to 240 Bloom, and in other embodiments, in the range of 140 to 200 Bloom.

In some embodiments, a matrix pellet of the invention are characterized as having a diameter size in the range of at least about 1-2 mm. In some embodiments, the diameter size of a matrix pellet can be in the ranges of at least about 0.5-1.0 mm, 1.0-1.5 mm, 1.5-2.0 mm, in certain embodiments the diameter may be in the range of at least about 2.0-2.5 mm, and 2.5-3.0 mm.

In further embodiments, a matrix pellet of the invention is characterized as having a weight in the range of at least about 0.5-5 mg. In some embodiments, the weight of a gelatin matrix pellet can be in the range of at least about 0.1-1 mg, 1-2 mg, 2-3 mg, 3-4 mg, 4-5 mg, 5-6 mg, 6-7 mg, 7-8 mg, 8-9 mg or 9-10 mg. In some embodiments, the weight may be in the range of about 0.5-5 mg, 1-4.5 mg, 1.5-4 mg, 2-3.5 mg or 2.5-3 mg.

In further embodiments, a matrix pellet of the invention is characterized as having a moisture content of up to about 15%, by weight (w/w). In some embodiments, the moisture content in a matrix pellet can be up to at least about 1%, 2%, 3%, 4%, 5%, 6%, 7%, 8%, 9%, 10%, 11%, 12, 13%, 14%, 15%

These particular structural features permit to obtain exceptionally high loading of the matrix (gelatin) pellets with an active ingredient, either a synthetic, semi-synthetic or natural cannabinoid, or a combination of a number of cannabinoids, or an extract of a cannabis plant, a combination of cannabis plant constituents, or a combination thereof.

In some embodiments, a matrix pellet of the invention can comprise an amount of an active ingredient that is up to about 30% (w/w). In some embodiments, the amount of an active ingredient comprised in a matrix pellet can be up to at least about 1%, 5%, 10%, 15%, 20%, 25% and 30% (w/w) or more, and further in the range of at least about 0.1-1%, 1-5%, 5-10%, 10-15%, 15-20%, 20-25%, 25-30% (w/w) or more.

In some embodiments, a matrix pellet of the invention may comprise (w/w):

Active ingredient(s)—up to 30%
Gelatin or a different matrix material—minimum 60%
Oil—up to 10% (or 35-45% of the active ingredients)
Water—up to 15%, and
Coloring agent—0.1-0.6% (or 0.3 mg), being optional.

It should be noted that linseed oil, castor oil and sesame oil are particularly used in some of the embodiments of the formulations. In some embodiments, the oil is Linseed oil (known to contain the essential nutrient Alpha-linolenic acid).

Castor oil is a source of ricinoleic acid, a monounsaturated, 18-carbon fatty acid. Among fatty acids, ricinoleic acid is unusual due to its hydroxyl functional group that makes it more polar than most fats and can synergies with gelatin. Sesame oil is compatible with cannabinoid and forms stable solutions.

Another important feature of the matrix pellets of the invention is their prolonged stability and shelf life at the room temperature, revealed in stability testing studies of gelatin beads containing CBD.

In some embodiments, a matrix pellet of the invention can ensure stability of an active ingredient for at least about 6 months or more at room temperature. More specifically, stability of an active ingredient comprised in a matrix pellet may be maintained for at least about 4-8, 8-12, 12-16, 16-20, 20-24, 24-28, 28-32, 32-36 months (e.g., up to 3 years).

In general, the technology used in accordance with the invention, e.g., of using a matrix pellet such as gelatin pellets, can be tailored for any lipophilic (poorly water soluble) drug to improve drug loading and high bioavailability, as well as user-friendly drug preparations. It is presently contemplated that this technology is particularly applicable to lipophilic drugs such as cannabinoids and cannabis-based medicines, i.e. cannabis extracts, combinations of cannabis plant constituents, or any combinations thereof.

As known in the art, 'cannabinoids' encompass a class of chemical compounds, cannabinoid/cannabinoid agonists/cannabinoid-related compounds, acting with various affinities on the endogenous cannabinoid receptors (CB1 and CB2). In accordance with aspects and embodiments of the invention, the term encompasses the group of ligands that include the endocannabinoids (produced naturally by humans and animals), phytocannabinoids (found in cannabis and some other plants), and synthetic cannabinoids (manufactured artificially). The most notable are tetrahydrocannabinol (THC) and cannabidiol (CBD).

CB1 receptors are found primarily in the brain, in the basal ganglia and in the limbic system, including the hippocampus, and also in the cerebellum and in both male and female reproductive systems. CB2 receptors are predominantly found in the peripheral nervous system and the immune system, or immune-derived cells with the greatest density in the spleen. Certain reports further indicate that CB2 is expressed by a subpopulation of microglia in the human cerebellum.

Clinical conditions that are treatable by cannabinoid/cannabinoid agonists/cannabinoid-related compounds include, for example, Anorexia, emesis, pain, inflammation, multiple sclerosis, neurodegenerative disorders (such as Parkinson's disease, Huntington's disease, Tourette's syndrome, Alzheimer's disease), epilepsy, spasticity, autism, tuberculosis, inflammatory bowel diseases, including ulcerative colitis and Crohn's disease, irritable bowel syndrome, glaucoma, osteoporosis, schizophrenia, cardiovascular disorders, cancer, obesity, and metabolic syndrome-related disorders, fibromyalgia, graft versus host disease, and may therefore be treated with formulations of the invention.

The term 'cannabinoids' also refers to the classical cannabinoids originating from, or mimicking, the natural cannabinoids in a viscous resin produced in glandular trichomes of a *cannabis* plant. At least 85 different cannabinoids have been isolated from various strains of *cannabis*, so far. The main classes of the classical cannabinoids are shown in Table 1 below.

TABLE 1

Main classes of natural cannabinoids

| Type | Skeleton |
| --- | --- |
| Cannabigerol-type CBG | |
| Cannabichromene-type CBC | |
| Cannabidiol-type CBD | |
| Tetrahydrocannabinol-and Cannabinol-type THC, CBN | |
| Cannabielsoin-type CBE | |
| iso-Tetrahydrocannabinol-type iso-THC | |

TABLE 1-continued

Main classes of natural cannabinoids

| Type | Skeleton |
|---|---|
| Cannabicyclol-type CBL | 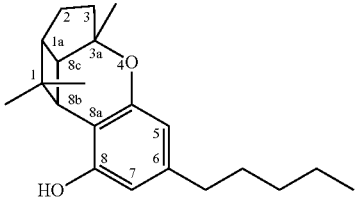 |
| Cannabicitran-type CBT | 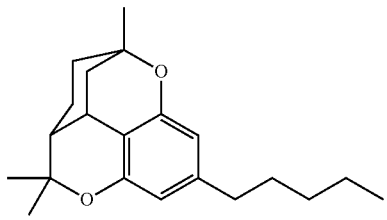 [SMILES: CCCCCc1cc2c3c(c1)OC(C)(C)C1CCC(C)(CC31)O2] |

Thus, in some embodiments of the invention, the matrix pellets of the invention may comprise, as an active ingredient, or as a combination of such actives, at least one of a Tetrahydrocannabinol and Cannabinol-type (THC, CBN), Cannabidiol-type (CBD), Cannabigerol-type (CBG), Cannabichromene-type (CBC), Cannabielsoin-type (CBE), iso-Tetrahydrocannabinol-type (iso-THC), Cannabicyclol-type (CBL), Cannabicitran-type (CBT), a derivative, a precursor, or a combination thereof. All classes derive from cannabigerol-type compounds and differ mainly in the way this precursor is cyclized. The classical cannabinoids are derived from their respective 2-carboxylic acids (2-COOH, also denoted with -A) by decarboxylation (catalyzed by heat, light, or alkaline conditions).

In some embodiments, the active is tetrahydrocannabinol or cannabidiol acid precursors, THC-A or CBD-A.

In some embodiments, the cannabinoids are selected from tetrahydrocannabinol (THC), cannabidiol (CBD) and cannabinol (CBN). A further selection of cannabinoids that may be used in accordance with the invention are as follows:
 THC (Tetrahydrocannabinol, including the two isoforms Δ9-THC, Δ8-THC and the acid form THC-A)
 CBD (Cannabidiol and the acid form CBD-A)
 CBN (Cannabinol)
 CBG (Cannabigerol)
 CBC (Cannabichromene)
 CBL (Cannabicyclol)
 CBV (Cannabivarin)
 THCV (Tetrahydrocannabivarin)
 CBDV (Cannabidivarin)
 CBCV (Cannabichromevarin)
 CBGV (Cannabigerovarin); and
 CBGM (Cannabigerol Monomethyl Ether).

Tetrahydrocannabinol (THC) refers to a synthetic or semi-synthetic or a natural cannabinoid, including delta-9-tetrahydrocannabinol (Δ9-THC) and delta-8-tetrahydrocannabinol (Δ8-THC), mimicking the action of the natural neurotransmitter, anandamide, and responsible for the majority of the effects associated with binding to CB1 cannabinoid receptors in the brain.

Cannabidiol (CBD) refers to a non-psychotropic cannabinoid having little affinity for CB1 and CB2 receptors but acts as an indirect antagonist of cannabinoid agonists. CBD has been shown to play a role in preventing the short-term memory loss associated with THC. It has been further associated with the relieve convulsion, inflammation, anxiety, and nausea in animal studies. CBD has shown antitumor activity on human breast carcinoma by inhibiting cancer cell growth.

Cannabinol (CBN) refers to the primary product of THC degradation, there is usually little of it in a fresh plant. CBN content increases as THC degrades in storage, and with exposure to light and air. It is only mildly psychoactive. Its affinity to the CB2 receptor is higher than for the CB1 receptor.

Cannabigerol (CBG) refers to a non-psychoactive cannabinoid. CBG has been shown to promote apoptosis in cancer cells and inhibit tumor growth. It acts as an α2-adrenergic receptor agonist, 5-HT1A receptor antagonist, and CB1 receptor antagonist. It also binds to the CB2 receptor.

Tetrahydrocannabivarin (THCV) is prevalent in certain central Asian and southern African strains of cannabis. It is an antagonist of THC at CB1 receptors and attenuates the psychoactive effects of THC.

Cannabidivarin (CBDV) is usually a minor constituent of a cannabinoid profile, enhanced levels of CBDV have been reported in feral cannabis plants from the northwest Himalayas, and in hashish from Nepal.

Cannabichromene (CBC) is non-psychoactive and does not affect the psychoactivity of THC. CBC has shown antitumor effects in breast cancer xenoplants in an animal model. It is more common in tropical cannabis varieties.

Thus, in some embodiments, a gelatin matrix pellet of the invention may comprise as an active ingredient at least one of THC, THCA, CBD, CBDA, CBN, CBG, CBC, CBL, CBV, THCV, CBDV, CBCV, CBGV, CBGM, a derivative, a precursor, or a combination thereof.

In further embodiments, particularly those concerning use of cannabinoids in the form of cannabis-based extracts of a cannabis plant or a combination of cannabis plant constituents, the matrix pellets of the invention may further comprise at least one of terpenes, sesquiterpenes, carotenes, flavonoids, or a combination thereof. These types of compounds may contribute to absorption, activity and further to flavor-, odor-, and color-imparting properties of the matrix pellets, in the sense of being more user-friendly and having high compliance.

In other embodiments, the matrix pellet of the invention may further comprise at least one antioxidants, absorption enhancers, color- and flavor-imparting agents, preservatives, stabilizers, salts, and/or combination(s) thereof.

Various sweeteners, taste modifiers, antioxidants, preservatives which are well known in the art may serve these purposes. For example, taste modifiers such as artificial sweeteners, flavorings as strawberry and peppermint oil, for example, and further plant sweeteners, sugars, honey, *Stevia*, steviol, glycosides, citrate, acids, menthol, anise, *eucalyptus* oil, fennel, natural antimicrobial substances and natural antioxidant (e.g. extracts of murta, oregano, rosemary, borage), antioxidants such as vitamins E (tocopherol) and C and their derivatives, butylated hydroxyanisole (BHA), butylated hydroxytolune (BHT) recognized as GRAS, and sulfides; any sweetener allowed for oral administration such as sugar, glucose, sucralose, cyclamate, sucrose, saccharin, fructose, maltose, *stevia* extract, sodium saccharine; salts such as NaCl, $NaHCO_3$, $Na_2CO_3$, citrate, and others.

Other additives may be used, such as nutrients, vitamins, antioxidants, various solidifiers and viscosity modifiers, such as stearic acid, ascorbyle palmitate, palmitic acid, or hexadecanoic acid, polymers, cetyl alcohol, cetostearyl alcohols, stearyl alcohol; and specific viscosity enhancers such as polyvinyl alcohol (PVA), sodium alginate, PG alginate, polyacrylic acids such as Carbopol, mucoadhesive polymers, Carbophils, cellulosescellulose-ethers such as hydroxypropylmethyl cellulose (HPMC), hydroxypropyl cellulose (HPC), hydroxyethyl cellulose (HEC), sodium carboxy methyl cellulose (Na-CMC), hyaluronic acid (HA), alginic acid, xanthan gum, pectins, carrageenan, Pluronics and Pluronic F127.

Amongst the many advantages of formulation and products of the invention, one particularly advantageous feature of the matrix pellet as a formulation has been revealed in quality control studies, showing capability thereof to exert controlled release and gastro-resistance with respect to dissolution of therein embedded actives.

Under the term 'controlled release' herein is meant a property or a modification enabling to achieve time dependent release, sustained release, prolonged release, and further pulse release, delayed release of the drug.

Under the term gastro-resistance' herein is meant a property or a modification enabling to achieve pH-controlled drug release, gastrointestinal targeting, colon delivery, protection of acid-sensitive actives, protection of gastric mucosa from aggressive actives. In this sense, gastro-resistance is also targeted drug release. It is further contemplated that for the purpose of certain embodiments, the matrix pellet, being optionally of gelatin, can further include a specific coating or other ingredients contributing to gastro-resistance and/or controlled release.

Improved gastro-resistance and/or controlled release can be achieved by modification of the matrix itself and/or coating of a matrix pellet using various pharmacological technologies, such as use of poly(meth)acrylates or layering. A well know example of poly(meth)acrylate coating which has been widely used in the pharmacological industry to achieve targeted and controlled drug release is EUDRAGIT®.

For layering, one or more substances are applied in layers to a core pellet (i.e. gelatin matrix pellet). The layering process is similar to a film coating process. When referring herein to layering is meant a range of technologies encompassing substances applied in layers to the core as a solution, suspension (Suspension/Solution layering) or powder (Dry powder layering). Further, various characteristics of the active substance layer can be achieved by adding suitable supplementary materials. Certain solid oils can be added to facilitate controlled release, such as mono, di and triglycerides oils, in general, and trilaurin, tricaprin, tripalmitin, trimyristin, glyceryl, hydrogenated palm oil distearate, hydrogenated castor oil, hydrogenated vegetable oil, in particular.

In other words, one of the additional unique features of the present technology is in providing a flexible product being adaptable to obtain enteric, protective or sustained-release properties for improved delivery of the active ingredient in terms of targeting, time, duration and exposure. To that end, for the purpose of some embodiments of the invention, the matrix pellets can further comprise or be coated with hydrophilic or hydrophobic polymers. In certain embodiments, matrix pellets of the invention can comprise matrix modifying/controlled release materials, which include, although not limited to, glycerides, waxes, fatty acids, methyl acrylate, methylmethacrylate, ethyl cellulose, poly(vinyl alcohol) (PVA), poly(vinyl pyrrolidone) (PVP), starch, polysaccharides, and others.

In some embodiments, the gelatin matrix pellets of the invention can be coated with hydroxypropyl methylcellulose, poly(meth)acrylates, methyl acrylate-methacrylic acid copolymers, cellulose acetate, polyvinyl acetate phthalate, and other types of coatings.

Considering the range of clinical indications to which the technology of the invention is applicable, it is contemplated that a matrix pellet of the invention may further comprise at least one additional therapeutic agent or a mineral, a nutrient, a vitamin, or a combination thereof.

A list of candidate therapeutic agents to be included in a matrix pellet of the invention may include, although not limited to, an antibiotic, anti-epileptic, anti-spastic, an anti-inflammatory, an analgesic, anti-anxiety, an antipsychotic agent. Further below is a more complete list of candidate therapeutic agents.

It is another important aspect of the invention to provide an oral solid cannabinoid dosage form comprising a plurality of matrix pellets comprising each (or at least a portion thereof) a pre-defined amount of an active ingredient selected from at least one synthetic, semi-synthetic or natural cannabinoid, an extract of a *cannabis* plant, a combination of *cannabis* plant constituents, and a combination thereof. One of the central advantages of the present technology, apart from its capability to achieve incorporation of high amounts of active ingredient(s) and high bioavailability, improved dosing efficiency, and no delivery system side effects, is the capacity to include one active ingredient in one pellet or several active ingredients in one single pellet or in different pellets that are further mixed afterwards in the same capsules without contact (multi-dose platform).

Thus, it is contemplated that in certain embodiments an oral solid cannabinoid dosage of the invention may comprise a plurality of gelatin matrix pellets comprising the same active ingredient defined as at least one synthetic, semi-synthetic or natural cannabinoid, an extract of a *cannabis* plant, a combination of *cannabis* plant constituents, or a combination thereof.

In other embodiments, an oral solid cannabinoid dosage of the invention may comprise a plurality of gelatin matrix pellets comprising distinct active ingredients defined as above. The term 'plurality' is meant to convey any number of gelatin matrix pellets (beads) in the range of at least about 50-400 beads, and more specifically, 50-100, 100-150, 150-200, 200-250, 250-300, 300-350 and 350-400 beads or more. The plurality may be further construed as a population of the same or different groups of matrix pellets according to the invention. In this connection, groups of pellets or populations are characterized with certain constitution, in terms of size, form, type of gelatin, type of active ingredient, dosage thereof, and further, matrix modifying/controlled release or coating material.

Thus, in certain embodiments, an oral solid cannabinoid dosage of the invention can comprise a plurality of matrix pellets of the same constitution. In other embodiments, an oral solid cannabinoid dosage of the invention can comprise a plurality of matrix pellets of distinct constitutions.

In other embodiments, an oral solid cannabinoid dosage form of the invention comprises gelatin matrix pellets with at least one of the following features:

(i) a diameter size in the range of at least about 1-2 mm, as referred to above, (ii) a weight in the range of at least about 0.5-5 mg, as referred to above, and/or (iii) a moisture content of up to about 15%, (w/w), as referred to above.

Owing to its particular formulation, i.e. as being composed of gelatin matrix pellets of the invention, an oral solid cannabinoid dosage of the invention can comprise a pre-defined amount of total active ingredients up to about 30% (w/w). In some embodiments, the amount of an active ingredient comprised in an oral cannabinoid dosage form may be up to at least about 1%, 5%, 10%, 15%, 20%, 25% and 30% (w/w) or more, and further in the range of at least about 0.1-1%, 1-5%, 5-10%, 10-15%, 15-20%, 20-25%, 25-30% (w/w) or more. Exemplary embodiments of this particular feature have been demonstrated in oral solid cannabinoid dosage forms containing two alternative doses of CBD, 10 mg and 100 mg and in a 50 mg dosage from, as further detailed hereinbelow.

It is thus contemplated that an oral solid cannabinoid dosage form of the invention can comprise a pre-defined total amount of active ingredients that is up to about 250 mg per dosage form. In some embodiments, the dosage form of the invention can comprise a pre-defined total amount of active ingredients in the ranges of at least about 0.1-1 mg, 1-10 mg, 10-50 mg, 50-100 mg, 100-150 mg, 150-200 mg, 200-250 mg, or more than 250 mg.

In some embodiments, an oral solid cannabinoid dosage form of the invention can comprise a pre-defined total amount of active ingredients that is in the range of at least about 90-110% of label claim.

Oral solid cannabinoid dosage forms of the invention may be packaged in various optional forms, such as capsules, being one of the most popular and convenient methods of drug delivery. In some embodiments, the oral solid cannabinoid dosage forms of the invention can be packaged in a two-piece hard capsule, optionally a capsule conferring gastro resistance. As noted hereinabove, a matrix pellet, such as a gelatin pellet, in itself can be coated with a gastro-resistant coating. A number of GRAS-based (Generally Regarded As Safe) materials that are known in the art can serve this purpose.

In other embodiments, the oral solid cannabinoid dosage forms of the invention can be packaged in a bag or a bottle ready to mix with food. Primary package can be opaque. In further embodiments, the solid cannabinoid dosage forms can use a secondary package, such as a blister (PVC/PVDC-Alufoil), a bottle, an aluminum pouch, others.

It should be appreciated that one of the particular features of an oral solid cannabinoid dosage form of the invention is that it can ensure room temperature stability of an active ingredient for at least about 4 months or more.

The invention provides gelatin matrix pellets and oral solid cannabinoid dosage forms of comprising as an active ingredient at least one of a THC- and CBN-type, a CBD-type, a CBG-type, a CBC-type, a CBE-type, a iso-THC-type, a CBL-type, a CBT-type, a derivative, a precursor, an acid form, and a combination thereof. In some embodiments, the oral solid cannabinoid dosage forms of the invention can comprise as an active ingredient one or more of THC, THCA, CBD, CBDA, CBN, CBG, CBC, CBL, CBV, THCV, CBDV, CBCV, CBGV, CBGM, a derivative, a precursor, or a combination thereof.

In some embodiments, the oral solid cannabinoid dosage forms of the invention can comprise one main active ingredient, being one main cannabinoid. Examples of such dosage forms have been presently demonstrated in producing capsules containing two optional doses of CBD, 10 mg and 100 mg. In some embodiments, the invention provides the following exemplary oral solid cannabinoid dosage forms:

10 mg CBD, 320.3 mg gelatin, 5.1 mg water, 4.3 mg hemp oil, 0.3 mg chlorophyllin-copper (green color, E141), packed in a two-piece hard capsules.

100 mg CBD, 290.3 mg gelatin, 17.7 mg water, 42.8 mg linseed oil 0.3 mg chlorophyllin-copper (green color, E141), packed in a two-piece hard capsules.

In other embodiments, the amount of a main cannabinoid can be in the range of at least about 0.1-0.5%, 0.1-1%, 0.1-2%, 0.1-3%, 0.1-4% and 1-5% of the total capsule (w/w), and further in the range of 1-10%, 1-20%, 1-30% of the total capsule (w/w), and more.

The term 'main cannabinoid' refers to a cannabinoid that is comprised in the oral solid cannabinoid dosage forms of the invention in an amount that is in the range of at least about 99.9-90% relative to the other cannabinoids (w/w), or in some embodiments, in the range of at least about 99.9-98.0%, 98.0-96.0%, 96.0-94.0%, 94.0-92.0% and 92.0-90.0% relative to the other cannabinoids (w/w), or broadly more than 50.0% of the other cannabinoids In some embodiments, the oral solid cannabinoid dosage forms of the invention can comprise an amount of other cannabinoids that is in the range of at least about 0.1-10% of the main cannabinoid (w/w). In some embodiments, these other cannabinoids can be present in the dosage forms of the invention in the range of at least about 0.1-0.5%, 0.5-1.0%, 1.0-1.5%, 1.5-2.0%, 2.0-2.5%, 2.5-3.0%, 3.0-3.5%, 3.5-4.0%, 4.0-4.5%, 4.5-5.0% and further 5-6%, 6-7%, 7-8%, 8-9% and 9-10%, or broadly up to 50.0%.

In some embodiments, this type of oral solid cannabinoid dosage forms can comprise as the main cannabinoid, THC or CBD, or can be significantly enriched in THC or CBD.

It is further contemplated that the present technology enables to include in the solid cannabinoid dosage forms of the invention a number of types of cannabinoids contributing or augmenting to their medicinal properties.

Thus, in some embodiments, oral solid cannabinoid dosage forms of the invention can comprise as an active ingredients two main types of cannabinoids. The amount of the two main cannabinoids, together, can be in the range of at least about 0.1-0.5%, 0.1-1%, 0.1-2%, 0.1-3%, 0.1-4% and 1-5% of the total capsule (w/w), and further in the range of 1-10%, 1-20%, 1-30% of the total capsule (w/w), and more.

In other words, the amount of the two main cannabinoids, together, may be in the range of at least about 99.9-90% of the other cannabinoids (w/w), and more specifically, in the range of at least about 99.9-98.0%, 98.0-96.0%, 96.0-94.0%, 94.0-92.0% and 92.0-90.0% of the other cannabinoids(w/w).

In some embodiments, it is contemplated that that in this types of the oral solid cannabinoid dosage forms of the invention, the ratio between the two main cannabinoids is in the ranges of at least about 1:1000 to 1:1, per weight or a molar ratio. In some embodiments, the ratio between the two main cannabinoids, per weight or molar, may be of in the range of at least about 1:1000 to 1:500, 1:500 to 1:200, 1:200 to 1:100, 1:100 to 1:50, 1:50 to 1:25, 1:25 to 1:10, 1:10 to 1:5, 1:5 to 1:1, and further, 1:2, 1:3, 1:4.

In some embodiments, the oral solid cannabinoid dosage forms of the invention may comprise THC and CBD, as the two main cannabinoids. In some embodiments, the oral solid cannabinoid dosage forms of the invention may comprise THC:CBD in a ratio that is at least about 1:1, 1:10, 1:50, 1:100, 1:1000 or more. In some embodiments, in some embodiments the ratio THC:CBD is 1:1, when a total amount in the range of at least about 0.1-0.5%, 0.1-1%, 0.1-2%, 0.1-3%, 0.1-4% and 1-5% of the total capsule (w/w), and further in the range of 1-10%, 1-20%, 1-30% and more of the total capsule (w/w).

In some embodiments, in the dosage forms THC is present in excess, wherein the ratio of THC:CBD, per weight or molar, is of at least about 2:1, 3:1, 4:1, 5:1, 10:1, 15:1, 20:1, 25:1, 30:1, 40:1, 50:1, 100:1 and more, when a total amount in the range of at least about 0.1-0.5%, 0.1-1%, 0.1-2%, 0.1-3%, 0.1-4% and 1-5% of the total capsule (w/w), and further in the range of 1-10%, 1-20%, 1-30% and more of the total capsule (w/w).

In some embodiments, the dosage forms comprises CBD in excess, i.e. the ratio of THC:CBD, per weight or molar, is at least about 1:2, 1:3, 1:4, 1:5, 1:6, 1:7, 1:8, 1:9, 1:10, and further 1:15, 1:20, 1:25, 1:30, 1:40, 1:50, 1:60, 1:70. 1:80, 1:90, 1:100, and still further 1:200, 1:300, 1:400, 1:500, and up to 1:1000 or more, when a total amount in the range of at least about 0.1-0.5%, 0.1-1%, 0.1-2%, 0.1-3%, 0.1-4% and 1-5% of the total capsule (w/w), and further in the range of 1-10%, 1-20%, 1-30% and more of the total capsule (w/w).

It should be noted that any dosage form of the invention, may comprise certain undesired or not-intended cannabinoids in trace or minor amounts that do not affect the integrity, stability or function of the dosage form. Trace or minor amounts may, for example be up to 5% w/w, relative to the main cannabinoid. These cannabinoids are not considered main active components or intended active components. These may be any of the cannabinoids that may be derived from the natural source from which the active component or main cannabinoid is derived. Impurities may be any one or more of THC, THCA, CBD, CBDA, CBN, CBG, CBC, CBL, CBV, THCV, CBDV, CBCV, CBGV, CBGM, a derivative, a precursor, or a combination thereof. In some cases, these trace amounts augment or contribute to medicinal properties of the oral solid cannabinoid dosage forms of the invention, without negatively affecting their physical or chemical parameters.

It is further contemplated that oral solid cannabinoid dosage forms of the invention, particularly those produced from *cannabis* extracts or *cannabis* plant constituents, can further comprise at least one of terpenes, sesquiterpenes, carotenes, flavonoids, or a combination thereof.

In some embodiments, oral solid cannabinoid dosage forms of the invention can comprise at least one of an antioxidant, a color- and a flavor-imparting agent, a preservative, a stabilizer, a salt, or a combination thereof.

In some embodiments, oral solid cannabinoid dosage form of the invention or capsules can be coated to facilitate gastro-resistance and/or controlled release. The terms 'gastro-resistance' and 'controlled release', as well as various types of coating and additives enabling to obtain such properties were previously mentioned. In this context, non-limiting examples of gastro resistant capsules include DRcap (hypromelose), i.e. coating with hydroxypropyl methylcellulose (HPMC) polymer.

It is further conceived that the same oral solid cannabinoid dosage can comprise various types of gelatin matrix pellets, in terms of distinct kinds of active pharmaceutical ingredients (API) in the form of distinct cannabinoids, as referred to herein, and further in terms of distinct types of coating, with or without coating, etc. In other words, according to the invention the capsule can comprise distinct gelatin matrix pellets of various cannabinoid types and contents, and of various coatings for controlled release and gastro-resistance. This can be tailored for specific needs of each patient, also referred to herein as a 'personalized approach'.

In further embodiments, oral solid cannabinoid dosage forms of the invention can further comprise at least one additional therapeutic agent or a mineral, a nutrient, a vitamin, or a combination thereof. This feature is particularly advantageous, as the present technology enables to combine in the same dosage form gelatin matrix pellets comprising lipophilic drugs with other pellets comprising non-lipophilic drugs.

Therapeutic agents that can be included in any dosage form of the invention may be any drug, or a combination, from one or more General Drug Categories classified by the FDA according to their clinical effects and applicability to common human disorders. Such drugs may be selected from analgesics, antacids, antianxiety drugs, antiarrhythmics, antibacterials, antibiotics, antimicotics, anticoagulants and thrombolyti cs, anticonvulsants, antidepressants, antidiarrheals, antiemetics, antifungals, antihistamines, antihypertensives, anti-inflammatories, antineoplastics, antipsychotics, antipyretics, antiviral s, barbiturates, beta-blockers, bronchodilators, cold cures, cholesterol lowering drugs, corticosteroids, cough suppressants, cytotoxics, decongestants, diuretics, expectorant, hormones, hypoglycemics, immune-suppressives, laxatives, muscle relaxants, sedatives, sex hormones, sleeping drugs, tranquilizer and vitamin supplements, such as omega fatty acids, omega-3-fatty acids, EPA, DHA, ALA.

In some embodiments, the dosage forms of the invention may comprise an antibiotic, anti-epileptic, anti-spastic, an anti-inflammatory, an analgesic, an antipsychotic agent.

It should be appreciated that the oral solid cannabinoid dosage forms of the invention may be presented in an oil, such as linseed oil, hemp oil, sesame oil, castor oil, chia (*Salvia hispanica* L.) seed oil, cotton oil, corn oil, olive oil, coconut oil, triglycerides, sunflower oil, soybean oil, canola oil.

It is yet another important aspect of the invention to provide a pharmaceutical solid cannabinoid dosage form for oral administration comprising a plurality of gelatin matrix pellets comprising a therapeutically effective amount of an active ingredient comprising at least one synthetic, semi-synthetic or natural cannabinoid, an extract of a *cannabis* plant, a combination of *cannabis* plant constituents, or a combination thereof, and further optionally comprising a pharmaceutically acceptable carrier, buffer, excipient.

Generally, the term 'therapeutically effective amount' refers to an amount of the active ingredient that induces a change in a condition treated by a dosage form of the invention, as measured by relevant definition criteria, being it changes in a condition monitored in an animal model or in a clinical setting. In this sense, the therapeutic effect is also a pharmacodymanic effect.

In some embodiments, a change in the condition being treated is identified if there is at least 5% improvement, or 10% improvement, or at least 25%, or at least 50%, or at least 75%, or at least 100% improvement. The change can be based on improvements in the severity of the treated condition in an individual, or on a difference in the frequency of improved conditions in populations of subjects with and without treatment with dosage forms of the invention, or with dosage forms of the invention in combination with other drugs.

A therapeutically effective amount (also pharmacologically or pharmaceutically or physiologically effective amount) also means an amount of active ingredient (a cannabinoid or a combination) that is needed to provide a desired level of active agent in the bloodstream or at a target organ of to provide an anticipated physiological response. The precise amount will depend upon numerous factors, e.g. type of an agent, activity of a composition, intended patient use (e.g. number of doses per day), patient considerations, and others, which can readily be determined by one skilled in the art. An effective amount of an agent can be administered in one administration, or through multiple administrations of an amount that total an effective amount, preferably within a 24-hour period. It can be determined using standard clinical procedures for determining appropriate amounts and timing of administration. It is understood that the effective amount can be the result of empirical and/or individualized (case-by-case) determination on the part of the treating health care professional and/or individual.

As noted above, in some embodiments a pharmaceutical oral dosage form of the invention can comprise a therapeutically effective amount of total active ingredients in the ranges of at least about 0.1-1 mg, 1-10 mg, 10-50 mg, 50-100 mg, 100-150 mg, 150-200 mg, 200-250 mg, and more. It should be further appreciated that in certain embodiments a pharmaceutical oral dosage form of the invention may comprise a therapeutically effective amount of a total active ingredient(s) in the ranges of at least about 250-300 mg, 300-350 mg, 350-400 mg, 400-450 mg, 450-500 mg, 500-550 mg, 550-600 mg and more than 600 mg per one administration or more than 1200 mg daily uptake.

The present pharmaceutical dosage forms may also be tailored such that a therapeutically effective amount of the total active ingredient(s) is personalized. In this context, the term 'personalized dose' refers to a method wherein the therapeutically effective dose is tailored to an individual patient based on the individual's predicted response and alleviation of symptoms of a disease and other consideration. Diagnostic testing can be employed for selecting appropriate and optimal therapies based on the context of a patient's molecular or biochemical analyses and other personalization measures (potentially including genetics). As such, the matrix technology is particularly advantageous, as various doses and cannabinoids combinations can be comprised in each bead, and a final dose is determined by packaging a suitable amount of beads and/or by mixing a suitable amount of beads from each type. The preparation can be done on-demand. Alternatively, beads can be prepared with more than one cannabinoid in the same bead. This personalized approach can be further extended to incorporate additional nutrients and therapeutic agents.

This feature of a personalized dosing is particular relevant to yet another important aspect of the invention, which is a kit comprising at least one container comprising a plurality of gelatin matrix pellets comprising a pre-defined amount of an active ingredient comprising at least one synthetic, semi-synthetic or natural cannabinoid, an extract of a *cannabis* plant, a combination of *cannabis* plant constituents, or a combination thereof. The kit is intended for achieving a controlled therapeutic effect, wherein each of the multiple components of the kit can be administered simultaneously or each of said multiple dosage forms can be administered sequentially in either order.

In some embodiments, the kit of the invention includes container means for containing separate compositions; such as a divided bottle or a divided foil packet. Separate compositions may also be contained within a single, undivided container. Typically the kit includes directions for administration of separate components. The kit form may be advantageous also when the separate components are administered in different dosage forms, or administered at different dosage intervals, or when titration of individual components is desired by the prescribing physician.

Thus, in certain embodiments the kit of the invention can comprise containers with the gelatin matrix pellets comprising distinct pre-defined amounts of an active ingredient.

In other embodiments the kit of the invention can comprise containers with gelatin matrix pellets comprising pre-defined amounts of distinct active ingredients.

In yet another aspect, the invention provides a controlled solid cannabinoid formulation for oral administration comprising a plurality of gelatin matrix pellets comprising a pre-defined amount of an active ingredient comprising at least one synthetic, semi-synthetic or natural cannabinoid, an extract of a *cannabis* plant, a combination of *cannabis* plant constituents, or a combination thereof.

Figure 4:
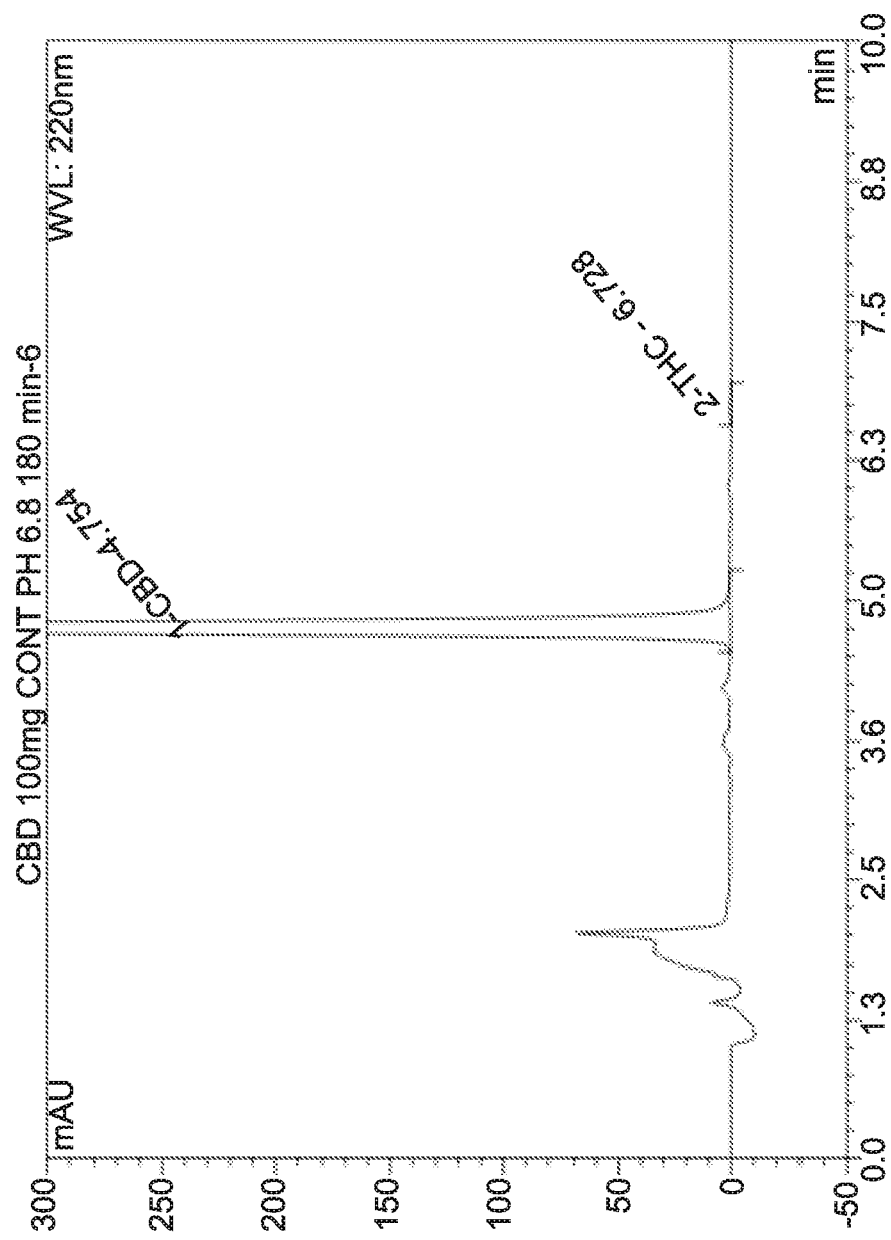
FIG. 4 shows a representative chromatogram of CBD dissolution from the gelatin matrix pellets of the invention (PTL101) containing 100 mg CBD at 180 min time point, wherein the pellets were incubated in simulated gastric fluid (pH 1.2) for 60 minutes and then in simulated intestinal fluid (0.1% SDS, pH 6.8) for additional 120 minutes. The diagram shows a major CBD peak and a negligible (<0.1% THC) peak detected at 220 nm.

The term 'controlled solid cannabinoid formulation' has been coined herein to convey the particular properties of the formulation of the invention revealed in (a) preferential intestinal release or dissolution of actives and/or (b) gastro-resistance. These two properties are not necessarily mutually dependent in nature, but can be additive and contributing factors. This latter point is exemplified in the dissolution studies showing not only more rapid dissolution of CBD from the presently developed CBD formulations in the simulated intestinal fluid than in the gastric fluid (Tables 8-10), but also that during gastric-intestinal transition CBD remained stable with only negligible traces of CBD to THC degradation (FIG. 4). Conversion of CBD to THC is well documented, especially for CBD exposed to an acidic environment.

Thus, in certain embodiments, the formulation of the invention can be articulated as a gastro-resistant solid cannabinoid formulation for oral administration comprising a plurality of gelatin matrix pellets comprising a pre-defined amount of an active ingredient comprising at least one synthetic, semi-synthetic or natural cannabinoid, an extract of a *cannabis* plant, a combination of *cannabis* plant constituents, or a combination thereof.

In other embodiments, the formulation of the invention is an oral controlled solid cannabinoid formulation comprising a plurality of gelatin matrix pellets comprising a pre-defined amount of an active ingredient comprising at least one synthetic, semi-synthetic or natural cannabinoid, an extract of a *cannabis* plant, a combination of *cannabis* plant constituents, or a combination thereof, wherein said controlled formulation provides a preferential intestinal release of the active ingredient.

The term 'preferential' herein denotes more rapid intestinal release of the cannabinoid relative to gastric release under in vitro conditions mimicking thereof, specifically when comparing the dissolution values of active in an 'intestinal fluid' to those in a 'gastric fluid' or in buffers mimicking thereof as 50%, 60%, 70%, 80%, 90% and more than 90% dissolution during the period of 10-20 min, 20-30 min, 30-40 min, 40-50 min, 50-60 min, 60-90 min, 90-120 min, 120-180 min.

The presently exemplified dissolution analysis of the 50 mg CBD and 100 mg CBD dosage forms has demonstrated, for both, up to 90% release of active in the first 30 min in the intestinal fluid, which attests to high bioavailability of these formulations. Although dissolution rate and bioavailability are not identical, there is generally a good linear relationship between these two properties. The bioavailability of the formulations of the invention can be estimated, for example, in terms of active dissolution up to 50%, 60%, 70%, 80%, 90% and more than 90% dissolution during the period of 10, 20, 30, 40, 50 and 60 min in the intestinal fluid.

From yet another, a broader, point of view, the formulation of the invention can be articulated in terms of these combined properties, namely a dual controlled oral solid formulation comprising a plurality of gelatin matrix pellets comprising a pre-defined amount of an active ingredient comprising at least one synthetic, semi-synthetic or natural cannabinoid, an extract of a *cannabis* plant, a combination of *cannabis* plant constituents, or a combination thereof, wherein the dual control comprises high bioavailability and gastro-resistance.

Another interesting feature of the instant controlled solid cannabinoid formulation is revealed in the total active ingredient blood exposure is in the range of at least about 1-48 hours, depending the amount of an active ingredient, as referred to above. Certain examples of blood exposure of CBD beads with various CBD contents have been presently demonstrated (FIGS. 1-4).

A total active ingredient blood exposure can be up to at least about 1, 2, 3, 4, 5, 6, 7, 8, 9, 10, 11, 12 hours, and further up to 18, 24, 30, 36, 42, and 48 hours or more, depending the amount of an active ingredient, as referred to above.

In yet another aspect, the invention provides a method for preparing gelatin matrix pellets comprising a pre-defined amount of an active ingredient comprising at least one synthetic, semi-synthetic or natural cannabinoid, an extract of a *cannabis* plant, a combination of *cannabis* plant constituents, or a combination thereof. The method of the invention permits production of solid gelatin matrix pellets described above.

In some embodiments, the method of the invention comprises:
(a) adding an amount of an active ingredient to a gelatin solution to obtain a mixture; and
(b) pelletizing said mixture to form gelatin matrix pellets.

In some embodiments, the method of the invention comprises:
(a) adding a pre-defined amount of the active ingredient to a gelatin solution to obtain a mixture; andp
(b) pelletizing said mixture in a cooling fluid and/or liquid to form gelatin matrix pellets.

In some embodiments, the method of the invention comprises:
(a) adding a pre-defined amount of the active ingredient to the hot gelatin solution to obtain a mixture; and
(b) pelletizing said mixture by dropping the mixture into a cooling fluid and/or liquid to form gelatin matrix pellets.

In some embodiments, the method of the invention comprises:
(a) obtaining a hot gelatin solution;
(b) adding a pre-defined amount of the active ingredient to the hot gelatin solution to obtain a mixture;
(c) homogenizing the mixture, e.g., by stirring;
(d) pelletizing the homogenous mixture to form gelatin matrix pellets.

In some embodiments, the method further comprises a step of filtering off the pellets.

In other embodiments, the method further comprises a step of removing residual cooling liquid by washing away with an organic solvent, with a centrifuge or with an air stream or (inert) gas stream.

In other embodiments, the method further comprise a step of drying the pellets in vacuum or in an oven or over desiccant.

In other embodiments, the gelatin solution is heated to a temperature between 25° C. and 80° C. In other embodiments, the gelatin solution is heated to a temperature between 30° C. and 70° C.

In other embodiments, where homogenizing the gelatin mixture is needed, it can be achieved by stirring.

In some embodiments, an active ingredient can be pre-dissolved in an oil, such as organic oils or oils comprising at least one lipid or a triglyceride prior to mixing into the gelatin or matrix material. Non-limiting examples of such oils include linseed oil, sesame oil, olive oil, castor oil, chia (*Salvia hispanica* L.) seed oil, cotton oil, corn oil, coconut oil, a medium chain triglyceride, a long chain triglyceride, sunflower oil, soybean oil, canola oil.

In some embodiments, the active ingredient is pre-dissolved in hemp oil.

In other embodiments, in addition to an active ingredient, other constituents can be added to the hot gelatin solution, such as additives, auxiliary materials and/or colorants.

In some embodiments, the step of cooling the homogenous mixture can use a cooling fluid in gas or liquid form such as an oil, an aqueous solution or a liquid gas.

In some embodiments, the cooling liquid can be a vegetable oil. Non limiting examples of vegetable oils include cotton seed oil, safflower oil, peanut oil, linseed oil, corn oil, olive oil, rapeseed oil, sesame oil, sunflower oil, soybean oil, wheat germ oil, castor oil, hydrogenated castor oil and any mixtures thereof.

In other embodiments, the cooling liquid can be a derivative of at least one lipid extracted from at least one plant. Specific examples of such liquids include, although not limited to, a derivative of a vegetable oil or a vegetable fat.

In some embodiments, the cooling liquid can be mono, di or triglyceride.

In some embodiments, the cooling liquid can be small chain, medium chain or long chain triglyceride.

In some embodiments, the cooling liquid can be an aqueous solution, such as brine solution.

In some embodiments, the cooling liquid is cooled to less than 15° C.

Once formed, the gelatin matrix pellets can be filtered off. The residual cooling liquid can be removed by different methods. By way of an example, it can be washed away with an organic solvent, removed with a centrifuge or by gas stream such as an air stream. Thereafter, the pellets can be dried, for instance in vacuum, in an oven or over desiccant. Before packaging, the pellets are usually sieved.

It should be appreciated that the invention further provides a line of products produced by the above methods, characterized in terms of uniformity of content and prolonged stability at the room temperature (see Tables 3-4)

In a further aspect the invention provides use of a plurality of gelatin matrix pellets comprising a pre-defined amount of an active ingredient comprising at least one synthetic, semi-synthetic or natural cannabinoid, an extract of a *cannabis* plant, a combination of *cannabis* plant constituents, or a combination thereof, for manufacture/preparation of a solid cannabinoid dosage form for oral administration.

In still another aspect the invention provides an oral solid cannabinoid dosage form comprising a plurality of gelatin matrix pellets comprising a therapeutic amount of an active ingredient comprising at least one synthetic, semi-synthetic or natural cannabinoid, an extract of a *cannabis* plant, a combination of *cannabis* plant constituents, or a combination thereof for use in a method of treating at least one symptom of a disease in a subject in need thereof.

The invention further provides a method for treating at least one symptom of a disease or a disease in a subject in need thereof, the method comprising administering to said subject an oral solid cannabinoid dosage form comprising a plurality of gelatin matrix pellets comprising a therapeutically amount of an active ingredient comprising at least one synthetic, semi-synthetic or natural cannabinoid, an extract of a *cannabis* plant, a combination of *cannabis* plant constituents, or a combination thereof.

It should be appreciated that the therapeutic method of the invention is applicable to a wide range of human diseases, including inflammatory, neurological, psychiatric disorders, malignancies and further immune, metabolic disorders, nutritional deficiencies, infectious diseases, and types of gastrointestinal disorders, cardiovascular disorders, and various types of pain, including chronic and neuropathic pain.

Considering the present level of knowledge regarding clinical applications of cannabinoids in young and elderly patients, it is conceived the instant cannabinoid dosage forms may be applicable, although not only, to at least one of depression, sleeping disorders, eating disorders, cancer, multiple sclerosis, graft versus host disease (GVHD), Parkinson's, epilepsy, autism, tuberculosis, ulcerative colitis, morbus Crohn, inflammatory bowel disorder (IBD), irritable bowel syndrome (IBS), appetite stimulant, appetite depressant, obesity, nausea, neuropathic pain, anxiety, Alzheimer's disease, amyotrophic lateral sclerosis (ALS), gastrointestinal disorders, hypertension, incontinence, pruritus, arthritis, arthrosis, rheumatic inflammation, insomnia, mycosis, local and/or chronic pain, inflammation, attention deficit and hyperactivity disorder (ADDH), vomiting, atopic dermatitis, fibromyalgia, AIDS, mood disorders, erectile dysfunction, premature ejaculation, nutritional deficiency.

It should be appreciated that the instant dosage forms and methods using thereof are equally applicable to subjects that are infants, adolescents or adults, humans or non-humans.

The terms 'treating', 'treatment' or 'therapy' as used herein refer equally to curative therapy and ameliorating therapy. The term includes an approach for obtaining beneficial or desired therapeutic effect, which may be established clinically by means of physiological, metabolic or biochemical parameters. In this application of invention, beneficial or desired clinical results include, but are not limited to, alleviation of symptoms, diminishment of extent of disease, stabilized (i.e., not worsening) condition, delay or slowing of progression or worsening of condition/symptoms, amelioration or palliation of a condition or a symptom, and remission (whether partial or total), whether detectable or undetectable. The term 'palliation' and any variations thereof, as used herein, means that the extent and/or undesirable manifestations of a physiological condition or a symptom are lessened and/or a time course of progression is slowed or lengthened, as compared to not administering compositions of the present invention. It should be further appreciated that for the present purpose this term also refers to an individualized therapeutically effective amount. Methods for establishing to an individualized therapeutically effective amount were mentioned. One common method is by 'trial and error' starting from a minimal or a standard dose, under the supervision of a treating physician.

Still further, it is conceived that in some embodiments the therapeutic methods of the invention can involve combination therapies. In other words, that the oral dosage forms and pharmaceutical compositions of the invention can be administered in combination with one or more additional compounds or therapies, the latter using enteral or parenteral and include, but are not limited to, intradermal, intramuscular, intraperitoneal, intravenous, subcutaneous, intranasal, epidural, and oral administration routes. The time period is preferably less than 72 hours, such as 48 hours, for example less than 24 hours, such as less than 12 hours, for example less than 6 hours, such as less than 3 hours. These terms may also mean that compositions of the invention and the additional therapeutic agent are administered together.

The invention further provides a therapeutic formulation comprising a plurality of gelatin matrix pellets according to the invention, a medicament comprising a plurality of gelatin matrix pellets according to the invention and methods of using each.

As may be understood, the invention generally provides basis for methods of treating or preventing any disease or condition that is treatable or preventable by at least one cannabinoid material, as defined and exemplified herein, by administering gelatin matrix pellets according to the invention as such or formulated into a dosage form, oral formulation or otherwise any therapeutic formulation to thereby achieve treatment or prophylaxis of at least one diseased, condition or symptom associated therewith.

Some embodiments of the invention will be now described by way of example with reference to accompanying Figures.

EXAMPLES

Method for Producing Solid Dosage Forms of the Invention

Cannabinoid gelatin pellets are prepared using a drop manufacturing process that includes the following steps:
(a) heating gelatin and water to obtain a hot gelatin solution (30° C. to 70° C.);
(b) adding a cannabinoid or a mixture of cannabinoids in an oil and a coloring agent to the solution to obtain a mixture;
(c) homogenizing the mixture by stirring;
(d) dropping the homogenous gelatin mixture into cooling liquid to obtain gelatin matrix pellets;
(e) filtering the gelatin matrix pellets off;
(f) removing the residual cooling liquid by means of an air stream;
(g) drying the gelatin matrix pellets;
(h) packing the gelatin matrix pellets into two-piece hard gastro-resistant capsules.

Example 1

Exemplary CBD Formulations

Two lead preparations of CBD solid dosage forms have been developed and included in the following Phase 1 clinical trial:
1. 10 mg CBD, 320.3 mg gelatin, 5.1 mg water, 4.3 mg hemp oil 0.3 mg chlorophyllin-copper (green color, E141), packed in a two-piece hard gastro-resistant capsules (designated PTL101-10 mg CBD of the invention).
2. 100 mg CBD, 290.3 mg gelatin, 17.7 mg water, 42.8 mg linseed oil, 0.3 mg chlorophyllin-copper (green color, E141), packed in a two-piece hard gastro-resistant capsules (designated PTL101-100 mg CBD of the invention).

Example 2

Clinical Studies in Humans

Figure 2:
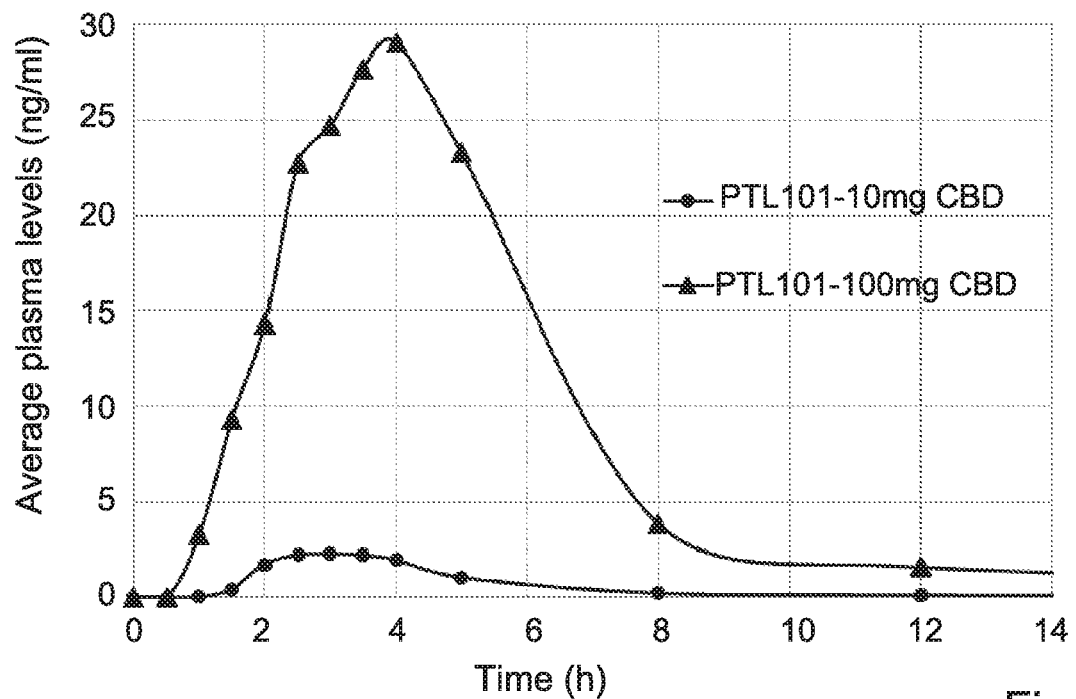
FIG. 2 demonstrates another advantageous feature of CBD gelatin matrix pellets of the invention (PTL101) revealed in higher drug loading capacity, when comparing mean CBD plasma levels following oral administering to healthy volunteers (N=14) at two doses, 10 mg CBD (●) and 100 mg CBD (▲).
Figure 3:
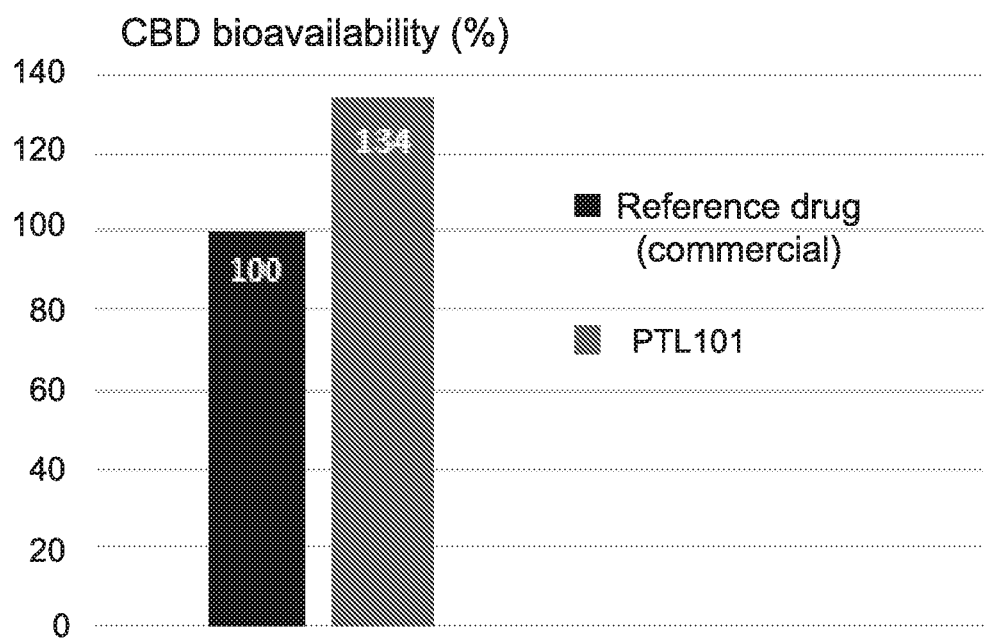
FIG. 3 demonstrates enhanced bioavailability of CBD gelatin matrix pellets of the invention (PTL101) (grey) compared to the commercial reference (Sativex, black), when administered to healthy volunteers (N=14). Relative bioavailability as was calculated from the ratios of Area Under concentration-time Curve (AUC) normalized to dose.

Phase 1 clinical trial has been conducted to assess pharmacokinetic (PK) properties of the above solid dosage forms containing CBD, 10 and 100 mg, in 14 healthy volunteers. Representative results of this are shown in FIGS. 1-3 and Table 2, while comparing pharmacokinetics and bioavailability of 10 mg and the 100 mg dosage forms of the invention and reference commercial drug (Sativex) containing the same amount of CBD.

TABLE 2

Summary of pharmacokinetics parameters

| Treatment | CBD Dose (mg) | Cmax (ng/ml) | Tmax (h) | AUCo-t (ng/ml*h) |
| --- | --- | --- | --- | --- |
| PTL101 | 10 | 2.97 [2.50; 3.54] | 2.97 [2.35; 3.75] | 8.89 [7.49; 10.55] |
| PTL101 | 100 | 43.42 [36.47; 51.69] | 3.45 [2.73; 4.36] | 144.77 [121.76; 172.14] |
| Sativex | 10 | 1.80 [1.51; 2.15] | 2.92 [2.31; 3.69] | 6.65 [5.59; 7.91] |

In summary, results of the Phase 1 human study demonstrated significantly higher CBD plasma levels in PTL101 of the invention compared to the commercial standard CBD preparation, Sativex, and further demonstrated superiority of PTL101 in terms of pharmacokinetic values and bioavailability. Consitent values of 134% higher bioavailability of CBD were obtained for PTL101 compared to Sativex. Further, this study demonstrated a significant dose response comparing PTL101 10 mg and 100 mg, which can translate to personalized clinical effect optimization.

Example 3

Quality Testing Studies

Representative results demonstrating additional characteristics of PTL101 are shown in Tables 3-4. Due to its unique structural properties and unique manufacture process, PTL101 maintained all the structural and functional features of cannabinoids.

Table 3 shows a uniformity of content in the fill weight of CBD containing gelatin matrix pellets and in the recovery of CBD at a level about 95-105% and at relative standard deviation of less than 1%. Capsules were dissolved within less than 30 minutes.

TABLE 3

Quality tests results of two batches of PTL101

| | Tests | | | | | |
| --- | --- | --- | --- | --- | --- | --- |
| | Uniformity of weight content in mg (N = 10) | | Assay CBD recovery % (n = 6) | | Disintegration (n = 6) | |
| Beads quality tests | Specification | Results | Specification | Results | Specification | Results |
| 10 mg CBD Lot# GP10-PT01 | Each capsule fill weight is between 314.5 to 365.5 mg (340 ± 7.5%) | Conforms Average: 340.8 Min: 337.0 Max: 343.1 | 90%-110% of label claim | Conforms Average: 99.5% RSD 0.4% | Capsule disintegrate completely in water in less than 30 minutes | Conforms Max 13:15 minutes |
| 100 mg CBD Lot# GP100-PT02 | Each capsule fill weight is between 417.2 to 484.8 mg (451 ± 7.5%) | Conforms Average: 451.0 Min: 449.6 Max: 453.6 | | Conforms Average: 105.5% RSD 0.7% | | Conforms Max 12:05 minutes |

Example 4

Stability Testing Studies

Table 4 shows that PTL101 10 mg and 100 mg CBD are stable at room temperature for at least 7 months.

TABLE 4

Stability testing of PTL101

| Stability testing - CBD Beads | | Initial | 2-8° C. | | 25° C./60% RH | | | 40° C./75% RH |
|---|---|---|---|---|---|---|---|---|
| | | | 1M | 4M | 1M | 4M | 7M | 2M |
| CBD 10 mg Lot# GP10-PT01 GP00487 | Assay (% recovery) | 99.32 | 97.80 | 99.82 | 100.50 | 100.78 | 108.01 | |
| | | 100.01 | 96.00 | 102.29 | 100.20 | 99.61 | 99.99 | |
| | | 99.08 | 96.90 | 99.10 | 99.80 | 99.94 | 102.63 | |
| | | 99.91 | 96.40 | 99.55 | 99.20 | | | |
| | | 99.00 | 97.40 | 95.19 | 98.50 | | | |
| | | 99.41 | 96.30 | 99.87 | 97.40 | | | |
| | Mean | 99.46 | 96.80 | 99.30 | 99.27 | 100.11 | 103.54 | |
| | SD | 0.42 | 0.70 | 2.30 | 1.16 | 0.60 | 4.09 | |
| | RSD | 0.42 | 0.72 | 2.32 | 1.17 | 0.60 | 3.95 | |
| | | 105.53 | 95.50 | 106.69 | 100.40 | 98.09 | 100.56 | |
| | | 105.83 | 96.20 | 102.59 | 99.10 | 98.90 | 99.29 | |
| | | 106.46 | 95.80 | 104.64 | 99.70 | 98.50 | 99.93 | |
| CBD 100 mg Lot# GP100-PT02 GP00505 | Assay (% recovery) | 105.50 | 96.00 | 103.62 | 99.40 | | | |
| | | 105.58 | 94.40 | 105.44 | 98.80 | | | |
| | | 104.20 | 95.20 | 104.53 | 99.10 | | | |
| | Mean | 105.52 | 95.52 | 104.59 | 99.42 | 98.50 | 99.93 | |
| | SD | 0.74 | 0.65 | 1.42 | 0.57 | 0.41 | 0.64 | |
| | RSD | 0.70 | 0.68 | 1.36 | 0.57 | 0.41 | 0.64 | |

Example 5

The Leading PTL101 50 mg and 100 mg CBD Products

Further quality control studies of the two advantageous dosage forms, PTL101 50 mg and 100 mg CBD, are demonstrated in Tables 5-7, which attest to compatibility thereof with the rigorous European Pharmacopoeia standards.

TABLE 5

Uniformity of weight content (mass in mg) in PTL101 products

| 50 mg CBD capsule | | | | 100 mg CBD capsule | | | |
|---|---|---|---|---|---|---|---|
| 331.6 | 333.8 | 339.4 | 332.2 | 460.6 | 442.3 | 448.3 | 451.4 |
| 331.0 | 335.9 | 325.9 | 327.2 | 441.3 | 446.8 | 464.3 | 446.7 |
| 331.4 | 355.4 | 323.0 | 332.5 | 439.7 | 450.1 | 434.0 | 441.1 |
| 322.3 | 332.4 | 325.6 | 325.4 | 441.8 | 453.5 | 436.1 | 433.6 |
| 331.6 | 352.6 | 323.5 | 330.0 | 448.9 | 440.2 | 447.7 | 463.7 |
| Mean | 332.1 | | | Mean | 446.6 | | |
| RSD | 2.6 | | | RSD | 2.0 | | |

TABLE 6

Uniformity of dosage unit (% of label claim) in PTL101 products

| 50 mg CBD capsule | | 100 mg CBD capsule | |
|---|---|---|---|
| 95.1 | 94.3 | 98.0 | 114.3 |
| 93.9 | 94.5 | 109.8 | 98.5 |
| 94.4 | 93.7 | 98.2 | 97.7 |
| 93.8 | 94.4 | 98.0 | 99.2 |
| 94.3 | 94.7 | 98.3 | 98.2 |
| Mean | 94.3 | Mean | 101.0 |
| RSD | 0.5 | RSD | 5.9 |

TABLE 7

Water content in PTL101 products (% w/w)

| Capsule # | 50 mg CBD capsule | | 100 mg CBD capsule | |
|---|---|---|---|---|
| 1 | 1.80 | 2.83 | 0.93 | 1.46 |
| 2 | 1.16 | 2.66 | 1.38 | 2.64 |
| 3 | 1.62 | 1.83 | 1.50 | 2.73 |
| 4 | 1.48 | 0.97 | 2.85 | 2.56 |
| 5 | 1.89 | 2.13 | 2.33 | 1.68 |
| 6 | 1.02 | 2.02 | 1.51 | 1.65 |
| 7 | 3.39 | 2.44 | 1.43 | 4.19 |
| 8 | 1.30 | 1.81 | 2.22 | 1.71 |
| 9 | 1.14 | 1.41 | 1.96 | 1.62 |
| 10 | 0.98 | 0.80 | 2.46 | 1.42 |
| | Mean | 1.7 | Mean | 2.0 |
| | SD | 0.7 | RSD | 0.7 |

Further studies of CBD dissolution rates from PTL101 50 mg and 100 mg CBD products in buffers mimicking intestinal and gastric fluids in terms of pH and composition demonstrated surprisingly high and highly preferential dissolution of CBD in the intestinal fluid (Tables 8-10 below). This feature was independent of capsule coating and was demonstrated as attributable to gelatin matrix pellets/beads (Table 10). These findings in vitro show additional advantageous features of PTL 101 referred to herein by the terms 'controlled release' and 'gastro-resistance'.

TABLE 8

Dissolution of CBD from PTL101 in simulated intestinal fluid (0.1M SLS, pH 6.8)

CBD dissolution from the gelatin beads (% of label claimed)

| Time, min | #1 | #2 | #3 | #4 | #5 | #6 | Mean | SD |
|---|---|---|---|---|---|---|---|---|
| 50 mg CBD beads | | | | | | | | |
| 0 | 0.0 | 0.0 | 0.0 | 0.0 | 0.0 | 0.0 | 0.0 | 0.0 |
| 10 | 93.1 | 90.4 | 88.6 | 85.1 | 90.5 | 85.6 | 88.9 | 3.1 |
| 20 | 95.4 | 91.4 | 90.6 | 90.5 | 90.9 | 90.1 | 91.5 | 2.0 |
| 30 | 94.3 | 90.5 | 90.3 | 89.9 | 93.5 | 90.0 | 91.4 | 2.0 |
| 100 mg CBD beads | | | | | | | | |
| 0 | 0.0 | 0.0 | 0.0 | 0.0 | 0.0 | 0.0 | 0.0 | 0.0 |
| 10 | 79.9 | 83.4 | 80.1 | 81.7 | 81.6 | 80.9 | 81.3 | 1.3 |
| 20 | 88.5 | 91.7 | 89.8 | 91.2 | 90.0 | 90.5 | 90.3 | 1.1 |
| 30 | 89.7 | 82.7 | 90.9 | 91.4 | 90.6 | 90.1 | 89.2 | 3.3 |

TABLE 9

Summary of dissolution results in the intestinal fluid (0.1M SLS, pH 6.8, mean ± SD, N = 6)

CBD released (% of label claimed)

| | 50 mg CBD beads | | 100 mg CBD beads | |
|---|---|---|---|---|
| Time, min | Mean | SD | Mean | SD |
| 0 | 0.0 | 0.0 | 0.0 | 0.0 |
| 10 | 88.9 | 3.1 | 81.3 | 1.3 |
| 20 | 91.5 | 2.0 | 90.3 | 1.1 |
| 30 | 91.4 | 2.0 | 89.2 | 3.3 |

TABLE 10

Dissolution of CBD from PTL101 products, transition from simulated gastric fluid at fed conditions (buffer acetate, pH 4.5) to intestinal fluids (0.1M SDS, pH 6.8)

CBD released (% of label claimed)

| | | Capsule (n = 3) | | Beads (n = 6) | | | |
|---|---|---|---|---|---|---|---|
| | | 100 mg CBD | | 50 mg CBD | | 100 mg CBD | |
| Time, min | Medium | Mean | SD | Mean | SD | Mean | SD |
| 0 | Acetate | 0.0 | 0.0 | 0.0 | 0.0 | 0.0 | 0.0 |
| 15 | buffer, | 0.0 | 0.0 | 0.1 | 0.2 | 0.0 | 0.1 |
| 30 | pH 4.5 | 0.0 | 0.0 | 0.1 | 0.1 | 0.1 | 0.1 |
| 45 | | 0.0 | 0.0 | 0.1 | 0.1 | 0.1 | 0.0 |
| 60 | | 0.0 | 0.0 | 0.2 | 0.1 | 0.1 | 0.1 |
| 90 | 0.1M SDS, | 57.8 | 5.2 | 88.9 | 4.5 | 100.6 | 10.3 |
| 120 | pH 6.8 | 84.3 | 1.1 | | | | |
| 180 | | 89.0 | 0.3 | | | | |

Degradation of CBD was examined following transition from simulated stomach fast fluids (pH 1.2) to intestinal fluids, and following transition from simulated stomach fed fluids (pH 4.5) to intestinal fluids (pH 6.8 with the addition of 0.1% SDS as surfactant) using the PTL101 100 mg CBD product. Conversion of CBD to THC, and other cannabinoids, under exposure to an acid environment is well documented. The detected THC was below 0.1% from the labeled CBD (FIG. 4). No additional THC was measured. These studies demonstrated that the present formulations were protective for CBD, or gastro-resistant, both in fast and fed simulated gastric conditions.

The invention claimed is:

1. A gelatin matrix pellet comprising a pre-defined amount of an active ingredient in hemp oil or linseed oil, wherein said active ingredient is homogenously distributed in the absence of a water-miscible solvent, wherein said active ingredient comprises at least one synthetic, semi-synthetic or natural cannabinoid, an extract of a *cannabis* plant, a combination of *cannabis* plant constituents, or a combination thereof, said at least one cannabinoid is selected from the group consisting of Tetrahydrocannabinol (THC), Cannabidiol (CBD), Cannabinol (CBN), Cannabigerol (CBG), Cannabichromene (CBC), Cannabicyclol (CBL), Cannabivarin, (CBV), Tetrahydrocannabivarin (THCV), Cannabidivarin (CBDV), Cannabichromevarin (CBCV), Cannabigerovarin (CBGV), Cannabigerol Monomethyl Ether (CBGM), and a combination thereof, and wherein said gelatin matrix pellet is gastro-resistant and has a preferential intestinal dissolution.

2. The gelatin matrix pellet according to claim 1 characterized as having gelatin from a bovine or fish origin at Bloom 100 to 240.

3. The gelatin matrix pellet according to claim 1, wherein the pre-defined amount of the active ingredient is up to about 30% (w/w).

4. The gelatin matrix pellet according to claim 1, comprising at least one of THC and CBD.

5. A population of gelatin matrix pellets according to claim 1.

6. The population according to claim 5, wherein a portion of said gelatin matrix pellets comprises THC and a further portion of said gelatin matrix pellets comprises CBD.

7. The population according to claim 5, wherein a portion of said gelatin matrix pellets consists of THC and a further portion of said gelatin matrix pellets optionally consists of CBD.

8. The gelatin matrix pellet according to claim 1, wherein the active ingredient and the gelatin are inter-mixed throughout the volume of the pellet.

9. The gelatin matrix pellet according to claim 8, wherein the active ingredient is homogenously distributed in the solid gelatin matrix.

10. A therapeutic formulation comprising a plurality of gelatin matrix pellets according to claim 1.

11. The therapeutic formulation according to claim 10 being a solid cannabinoid dosage form for oral administration.

12. An oral solid cannabinoid dosage form comprising a plurality of gelatin matrix pellets according to claim 1.

13. The gelatin matrix pellet of claim 1, wherein the gastro-resistance is provided by a gastro-resistant coating of the gelatin matrix pellet.

14. An oral solid cannabinoid dosage form comprising a plurality of gelatin matrix pellets comprising a pre-defined amount of an active ingredient in hemp oil or linseed oil, wherein said active ingredient is homogenously distributed therein in the absence of a water-miscible solvent, wherein said active ingredient comprises at least one synthetic, semi-synthetic or natural cannabinoid, an extract of a *cannabis* plant, a combination of *cannabis* plant constituents, or a combination thereof, said at least one cannabinoid is selected from the group consisting of Tetrahydrocannabinol (THC), Cannabidiol (CBD), Cannabinol (CBN), Cannabigerol (CBG), Cannabichromene (CBC), Cannabicyclol (CBL), Cannabivarin, (CBV), Tetrahydrocannabivarin (THCV), Cannabidivarin (CBDV), Cannabichromevarin (CBCV), Cannabigerovarin (CBGV), Cannabigerol Monomethyl Ether (CBGM), and a combination thereof, and said oral cannabinoid solid dosage form is gastro-resistant and has a preferential intestinal dissolution, and wherein the gelatin matrix pellets are having at least one of:

(i) a diameter size in the range of at least about 1-2 mm,
(ii) a weight in the range of at least about 0.5-5 mg, and
(iii) a moisture content of up to about 15% (w/w).

15. The oral solid cannabinoid dosage form according to claim 14, comprising at least one of THC or CBD.

16. The oral solid cannabinoid dosage form according to claim 14, wherein the gelatin matrix pellets comprise the same active ingredient(s) or a combination of active ingredients.

17. The oral solid cannabinoid dosage form of claim 14, wherein the gastro-resistance is provided by a gastro-resistant coating of the oral dosage form.

18. A method for treating at least one symptom of a disease in a subject in need thereof, the method comprising administering to said subject an oral solid cannabinoid dosage form comprising a plurality of gelatin matrix pellets comprising a therapeutically amount of an active ingredient in hemp oil or linseed oil,
wherein said active ingredient is homogenously distributed therein in the absence of a water-miscible solvent,
wherein said active ingredient comprises at least one synthetic, semi-synthetic or natural cannabinoid as a main cannabinoid, the at least one synthetic, semi-synthetic or natural cannabinoid being selected from the group consisting of Tetrahydrocannabinol (THC), Cannabidiol (CBD), Cannabinol (CBN), Cannabigerol (CBG), Cannabichromene (CBC), Cannabicyclol (CBL), Cannabivarin, (CBV), Tetrahydrocannabivarin (THCV), Cannabidivarin (CBDV), Cannabichromevarin (CBCV), Cannabigerovarin (CBGV), Cannabigerol Monomethyl Ether (CBGM), and a combination thereof, an extract of a *cannabis* plant, a combination of *cannabis* plant constituents, or a combination thereof, and
wherein said oral cannabinoid solid dosage form is gastro-resistant and has a preferential intestinal dissolution.

19. The method according to claim 18, wherein the disease is at least one of an inflammatory disorder, a neurological disorder, a psychiatric disorder, a malignancy, an immune disorder, a metabolic disorder, a nutritional deficiency, an infectious disease, a gastrointestinal disorder, a cardiovascular disorder, a pain.

20. An oral solid cannabinoid dosage form comprising a plurality of gelatin matrix pellets, each pellet consisting of a gelatin matrix and at least one synthetic, semi-synthetic or natural cannabinoid, an extract of a *cannabis* plant, a combination of *cannabis* plant constituents or a combination thereof in hemp oil or linseed oil and water, and optionally an additive,
wherein the at least one synthetic, semi-synthetic or natural cannabinoid is selected from the group consisting of Tetrahydrocannabinol (THC), Cannabidiol (CBD), Cannabinol (CBN), Cannabigerol (CBG), Cannabichromene (CBC), Cannabicyclol (CBL), Cannabivarin, (CBV), Tetrahydrocannabivarin (THCV), Cannabidivarin (CBDV), Cannabichromevarin (CBCV), Cannabigerovarin (CBGV), Cannabigerol Monomethyl Ether (CBGM), and a combination thereof,
wherein the additive is selected from the group consisting of terpenes, carotenes, flavonoids, nutrients, vitamins, antioxidants, absorption enhancers, color- and flavor-imparting agents, preservatives, stabilizers, salts, solidifiers and viscosity modifiers and any combination thereof, and
wherein said oral cannabinoid solid dosage form is gastro-resistant and has a preferential intestinal dissolution.

* * * * *